United States Patent [19]
Yu et al.

[11] Patent Number: 6,039,954
[45] Date of Patent: Mar. 21, 2000

[54] HERBAL COMPOSITIONS FOR TREATMENT OF GASTROINTESTINAL DISORDERS

[75] Inventors: Yu Long Yu, Edensor Park; Alan Bensoussan, Lane Cove, both of Australia

[73] Assignee: Chinese Medicines Scientific Consultants Pty Ltd., Chatswood, Australia

[21] Appl. No.: 09/275,653

[22] Filed: Mar. 24, 1999

[51] Int. Cl.$^7$ ..................................... A61K 35/78
[52] U.S. Cl. ............................................. 424/195.1
[58] Field of Search ........................................... 424/195.1

[56] References Cited

U.S. PATENT DOCUMENTS

| | | | |
|---|---|---|---|
| 5,164,184 | 11/1992 | Kim | 424/195.1 |
| 5,466,452 | 11/1995 | Whittle | 424/195.1 |
| 5,470,589 | 11/1995 | Shi | 424/698 |
| 5,651,997 | 7/1997 | Makino et al. | 424/682 |

*Primary Examiner*—Raymond Henley, III
*Attorney, Agent, or Firm*—Fish & Richardson P.C.

[57] ABSTRACT

Herbal formulations are disclosed for the treatment of gastrointestinal disorders, in particular Irritable Bowel Syndrome (IBS). The compositions are formulated preferably with powdered herbs however combined extracts of herbs are also contemplated.

27 Claims, No Drawings

HERBAL COMPOSITIONS FOR TREATMENT OF GASTROINTESTINAL DISORDERS

FIELD OF THE INVENTION

This invention relates to new medicinal compositions and methods for treating gastrointestinal disorders, in particular the treatment of Irritable Bowel Syndrome.

BACKGROUND OF THE INVENTION

Irritable bowel syndrome (IBS) is a common functional bowel disorder accounting for a significant proportion of patients seen in gastroenterologly practice.[1] it is charecterised by chronic or recurrent abdominal pain and disturbed defecation. studies in the U.S.A. and Australia suggest that between 10% and 20% of the population suffer from this disorder.[2,3,4,5] There is no single treatment available that is reliably effective for this condition.[6,7] Patients use a variety of approaches to assist in its management including drugs, dietary modifications, counselling, and more recently Chinese herbal medicine (CHM).[8]

According to the fundamental principals of practice in traditional Chinese medicine, treatment should be tailored to the individual clinical presentation of patients, even though they may all have the same western medical diagnosis.[8,14,15] Furthermore, treatment needs to be modified at different stages of the patient's illness or recovery. However, such an approach to treatment of disease can be cumbersome and is not entirely compatible with conventional pharmaceutical and medical practice.

Thus, there is a need for effective standardised Chinese herbal medicinal preparations for the treatment of gastrointestinal disorders such as irritable bowel syndrome and for appropriately rigorous clinical study design for assessing their efficacy.

It is an object of the present invention to provide an effective treatment for gastrointestinal disorders, such as Irritable Bowel Syndrome (IBS), which would ameliorate at least some of the disadvantages of the prior art therapies and methods, or at least provide useful alternatives.

SUMMARY OF THE INVENTION

A Chinese herbal formulation disclosed herein for treatment of gastrointestinal disorders, in particular Irritable Bowel Syndrome (IBS), was compared against a placebo (made to taste, smell and look like Chinese herbs) using a randomised, double-blind, placebo controlled study design.

According to a first aspect there is provided a composition including the herbs *Ledebouriellae sesloidis, Supleurum chinense, Artemesiae capillaris, fraxini, plantaginis, Paeoniae lactiflorae* and *schizandrae*.

According to a second aspect there is provided a composition including any two herbs selected from the group consisting of *Codonopsis Pilosulae, Atractylodis Macrocephalae, Poriae Cocos* and *Glycyrrhizae Uralensis*, any two herbs selected from the group consisting of *Agastaches seu Pogostemi, Magnoliae Officinalis, Citri Reticulatae* and *Saussureae seu Viladimiriae*, any two herbs selected from the group consisting of *Phellodendri, Coptidis, Colcis Lachryma-jobi, Zingiberis Offinicinalis* and *Angelicae Dehuricae*, and any two herbs selected from the group consisting of *Ledebouriellae Sesloidis, Bupleurum Chinense, Artemesiae Capillaris, Fraxini, Plantaginis, Paeoniae Lactiflorae* and *Schizandrae*.

According to a third aspect there is provided a composition including the herbs *Codonopsis Pilosulae, Agastaches seu Pogostemi, Ledebouriellae Sesloidis, Coicis Lachryma-jobi, Bupleurum Chinense, Artemesiae Capillaris, Atractylodis Macrocephalae, Magnoliae Officinalis, Citri Reticulatae, Zingiberis, Offinicinalis, Fraxini, Poriae Cocos, Angelicae Dehuricae, Plantaginis, Phellodendri, Glycyrrhizae Uralensis, Paeoniae Lactiflorae, Saussureae seu Vladimiriae, Coptidis* and *Schizandrae*.

Preferably, the compositions are formulated with powdered herbs. If the moisture content of the herbs is high, the herbs can be baked before being powdered by for example grinding, or by other suitable means. Even more preferred are formulations which include extracts of the herbs. For such formulations each individual herb can be extracted either with water or an organic solvent (eg. alcohol) and the extracts combined in an appropriate formulation. Alternatively all the dry herbs can be combined, boiled together and then concentrated by spray drying or other means known in the art, into a dry granulated formulation.

Preferably, the compositions are prepared in a capsule dosage form, however it will be understood by those skilled in the art that other dosage forms may also be suitably prepared by known methods, for example tablets, powders, pastes, liquids and similar dosage forms. Also it will be understood that the compositions of the present invention may also contain one or more conventional pharmaceutically acceptable excipients, adjuvants, solvents or carriers and may also include flavours, colourings, coatings, etc.

According to a fourth aspect there is provided a method of treating gastrointestinal disorders including the administration to a subject requiring such treatment a composition according to any one of first to third aspects.

Preferably, the gastrointestinal disorder to be treated is Irritable Bowel Syndrome (IBS). The treatment is preferably administered orally and may be therapeutic or prophylactic. The treatment may be delivered in a single bolus dose, multiple doses or via a slow release device.

The term "herb" as used herein includes the whole herb or tuber, as well as the root, stem, flower or fruit of the herb.

DETAILED DESCRIPTION OF THE INVENTION

In a preferred embodiment of the invention, the composition of the invention includes a combination of any two herbs selected from Groups 1, 2 and 3 and any three herbs selected from Group 4, depicted in Table 5. The herbs may each be included in concentration of from 1% to 30% of the total weight of the herbal composition.

In another preferred embodiment the composition of the invention includes the herbs *Ledebouriellae Sesloidis, Bupleurum Chinense, Artemesiae Capillaris, Fraxini, Plantaginis, Paeoniae Lactiflorae* and *Schizandrae*, each herb included in a concentration of from 1% to 30%, the balance being made up for example by other herbs, preferably *Codonopsis Pilosulae, Agastaches seu Pogostemi, Coicis Lachryma-jobi, Atractylodis Macrocephalse, Magnoliae Officinalis, Citri Reticulatae, Zingiberis Offinicinalis, Poriae Cocos, Angelicae Dehuricae, Phellodendri, Glycyrrhizae Uralensis, Saussureae seu Vladirniriae* and *Coptidis*.

Although the administration of compositions including a selection of herbs from each of the four groups depicted in Table 5, or the key herbs discussed above and depicted in Table 6, are useful in the treatment of Irritable Bowel Syndrome, the synergism between all the herbs renders the administration of a combination containing each of the herbs mentioned desirable.

Thus, in a more preferred embodiment, the composition of the present invention includes each herb combined in the proportions given in Table 2.

In addition to providing for the first time an effective and well tolerated treatment for Irritable Bowel Syndrome, the availability of the herbs and ease of formulation (powdering, extraction, etc.) provides a less costly alternative medicament. The treatment may also be individualised as well as prepared as a standard formulation, making the treatment more broadly applicable and effective over both short and long term administration.

The invention will now be described with reference to the following examples to illustrate preferred embodiments only and does not serve to limit the invention.

EXAMPLE 1

Herbs and Preparation of Formulations

For the purpose of conducting a clinical study, all herbs were used in the dried powdered form and encapsulated before administration. If sufficiently dry, the herbs were powdered using a grinder or similar device. if the moisture content of the herbs was high, the herbs were baked before being powdered.

The components of the standard herbal formulation according to one embodiment of the present invention are listed in Table 1. The key herbs are listed in Table 2 and the grouping of the herbs for a particular selection according to one embodiment of the present invention is shown in Table 3. The placebo preparation was prepared and encapsulated by a pharmaceutical contractor. It was designed to taste, smell and look like a Chinese herb formula and, after testing an a number of independent volunteers, it was deemed indistinguishable from raw powdered Chinese herbs.

The herbs may also be formulated by one of the following methods:

(a) concentrating either a water or an organic solvent (eg. alcohol) extract of each herb and then combining the extracts;

(b) all the raw herbs can be boiled together and then concentrated by spray drying or other known methods into a dry granulated formulation. The extracts can be concentrated before or after combining and may be processed into tablets or capsules.

TABLE 1

Standard formula (capsule ingredients)

| Chinese name | Pharmaceutical name | Powdered herb |
| --- | --- | --- |
| Dang Shen | Codonopsis Pilosulae, radix | 7% |
| Huo Xiang | Agastaches seu Pogostemi, herba | 4.5% |
| Fang Feng | Ledebouriellae Sesloidis, radix | 3% |
| Yi Yi Ren | Coicis Lachryma-jobi, semen | 7% |
| Chai Hu | Bupleurum Chinense | 4.5% |
| Yin Chen | Artemesiae Capillaris, herba | 13% |
| Bai Zhu | Atractylodis Macrocephalae, rhizoma | 9% |
| Hou Po | Magnoliae Officinalis, cortex | 4.5% |
| Chen Pi | Citri Reticulatae, pericarpium | 3% |
| Pao Jiang | Zingiberis Offinicinalis, rhizoma | 4.5% |
| Qin Pi | Fraxini, cortex | 4.5% |
| Fu Ling | Poriae Cocos, sclerotium (Hoelen) | 4.5% |
| Bai Zhi | Angelicae Dehuricae, radix | 2% |
| Che Qian Zi | Plantaginis, semen | 4.5% |
| Huang Bai | Phellodendri, cortex | 4.5% |
| Zhi Gan Cao | Glycyrrhizae Uralensis, radix | 4.5% |
| Bai Shao | Paeoniae Lactiflorae, radix | 3% |
| Mu Xiang | Saussureae seu Vladimiriae, radix | 3% |
| Huang Lian | Coptidis, rhizoma | 3% |
| Wu Wei Zi | Schizandrae, fructus | 7% |

TABLE 2

Key herbs

| Chinese name | Pharmaceutical name | Powdered herb |
| --- | --- | --- |
| Fang Feng | Ledebouriellae Sesloidis, radix | 3% |
| Chai Hu | Bupleurum Chinense | 4.5% |
| Yin Chen | Artemesiae Capillaris, herba | 13% |
| Qin Pi | Fraxini, cortex | 4.5% |
| Che Qian Zi | Plantaginis, semen | 4.5% |
| Bai Shao | Paeoniae Lactiflorae, radix | 3% |
| Wu Wei Zi | Schizendrae, fructus | 7% |

TABLE 3

Herb combinations (any two herbs from group 1 can be combined with any two herbs from group 2, with any two herbs from group 3 with any three herbs from group 4)

| Chinese name | Pharmaceutical name | Powdered herb |
| --- | --- | --- |
| Group 1 | | |
| Dang Shen | Codonopsis Pilosulae, radix | 7% |
| Bai Zhu | Atractylodis Macrocephalae, rhizoma | 9% |
| Fu Ling | Poriae Cocos, sclerotium (Hoelen) | 4.5% |
| Zhi Gan Cao | Glycyrrhizae Uralensis, radix | 4.5% |
| Group 2 | | |
| Huo Xiang | Agastaches seu Pogostemi, herba | 4.5% |
| Hou Po | Magnoliae Officinalis, cortex | 4.5% |
| Chen Pi | Citri Reticulatae, pericarpium | 3% |
| Mu Xiang | Saussureae seu Vladimiriae, radix | 3% |
| Group 3 | | |
| Huang Bai | Phellodendri, cortex | 4.5% |
| Huang Lian | Coptidis, rhizoma | 3% |
| Yi Yi Ren | Coicis Lachryma-jobi semen | 7% |
| Pao Jiang | Zingiberis Offinicinalis, rhizoma | 4.5% |
| Bai Zhi | Angelicae Dehuricae, radix | 2% |
| Group 4 | | |
| Fang Feng | Ledebouriellae Sesloidis, radix | 3% |
| Chai Hu | Bupleurum Chinense | 4.5% |
| Yin Chen | Artemesiae Capillaris, herba | 13% |
| Qin Pi | Fraxini, cortex | 4.5% |
| Che Qian Zi | Plantaginis, semen | 4.5% |
| Bai Shao | Paeoniae Lactiflorae, radix | 3% |
| Wu Wei Zi | Schizandrae, fructus | 7% |

The concentrations of individual herbs depicted in Tables 1 to 3 may vary by about ±50%.

EXAMPLE 2

Selection and Recruitment of Patients

The majority of patients were recruited from gastroenterology units in two teaching hospitals in Sydney, Australia and through private gastroenterologists. Patient screening and subsequent review occurred in these centers. Patients were further diagnosed (according to Chinese medicine principles) and then treated by Chinese medicine practitioners.

All herbal medicines used were administered within standard dosage levels and are all available over the counter throughout Australia.

(i) Subjects

Patients between the ages of 18 and 75 (inclusive) were screened by a gastroenterologist. This involved a routine clinical work-up for IBS patients with tests as determined appropriate by the specialist, including a colonoscopy or barium enema in the last five years (for 18–60yrs) or within the previous 3 years (for 61–75yrs). Patients were assessed according to the Rome criteria, an established standard for diagnosis of IBS—(3 months continuous or recurrent abdominal pain/discomfort including some pain present within the last two weeks AND two of the following—altered stool frequency, altered stool form, altered stool passage, passage of mucous, and abdominal distension).[16,17] If diarrhoea was a prominent symptom lactose intolerance was excluded (by hydrogen breath testing or over a two week lactose exclusion period). A full list of inclusion and exclusion criteria are presented in Table 4.

TABLE 4

Inclusion and exclusion criteria

| Inclusion criteria | Exclusion criteria |
|---|---|
| 1. Age 18–75 years inclusive | • Pregnancy or breast feeding |
| 2. Colonic evaluation (colonoscopy or barium enema) within the previous 5 years (for 18–60 yrs) or within the previous 3 years (for 61–75 yrs) | • Liver disease<br>• Medications: anticholinergics, lactulose, smooth muscle relaxants, motility stimulants, antidepressants. |
| 3. IBS by criteria:<br>At least 3 months of continuous or recurrent symptoms of: | • Usage of these is accepted provided patient is still symptomatic of IBS, |
| • Abdominal pain or discomfort with at least some discomfort present within the last two weeks.<br>and<br>two or more of the following on at least one quarter of occasions or days: | medications have been used for 3 months, and effects of medications are stable.<br>• Current alcoholism or drug abuse<br>• Current psychiatric illness or dementia |
| i. abdominal distension that is visible or felt by tight clothing<br>ii. pain relief with bowel action<br>iii. more frequent stools with onset of pain<br>iv. looser stools with onset of pain<br>v. mucous in stools<br>vi. feeling of incomplete evacuation<br>4. At least one marking on the Visual Analogue Scales for IBS symptoms to be <u>at least 20 mm</u> from the 'not present' end of the scale.<br>5. Normal liver function tests and full blood count urea and creatinine (within the last two weeks) | • Allergies to food additives<br>• Lactose intolerance-no obvious clinical indications<br>• Inflammatory bowel disease (ulcerative colitis, Crohn's)<br>• Gastric and duodenal ulcers<br>• Cancers of the gastrointestinal tract<br>• Celiac disease<br>• Diabetes mellitus |

Written informed consent was obtained from all patients before entering the study. Patients were free to withdrew from the study at any time.

(ii) Treatment Schedule

After initial gastroenterological screening (Week 0) all patients entered a two week run-in period. A Bowel Symptom Scale (BSS) was completed at the beginning and end of the two week period to assess measurement reliability, and to account for any degree of improvement based simply on admission to the study. Patients were seen on specified days by one of three herbalisls during the study period and were not permitted to change herbalist during the course of the treatment. The first consultation with the Chinese herbalist occurred at Week 2, at which time the patient was randomised (by an assistant) into placebo or standard treatment groups. The patient was reviewed by the Chinese herbalist at fortnightly intervals an two occasions and then monthly intervals on two further occasions. Sixteen weeks continuous treatment was administered. All patients were reviewed by their gastroenterologist after eight weeks of treatment (and precautionary liver function tests performned), and reviewed again at the end of the 16 week treatment period.

Patients were closely monitored for an side effects or worsening of symptoms. Follow-up questionnaires were sent to all patients 14 weeks after completion of the treatment period. Tratment codes were only broken and revealed to patients after completion of the follow-up questionnaires.

(iii) Herbal Preparation and Dispensing

All herbs and the placebo formulation used in the clinical study were supplied in the same opaque capsules. Patients in both groups were required to take the same dosage levels (5 capsules thrice daily). All patients were treated in an equivalent fashion. Compliance was assessed by an item included in the Bowel Symptom Scale (BSS) and by pill count.

EXAMPLE 3

Assessment and Data Analysis (i) The Bowel Symptom Scale (BSS)

The BSS was designed as the major instrument to assess change in IBS symptoms during the course of the treatment. It consists of visual analogue scales related to each individual symptom and an overall severity scale. Both patients and gastroenterologists were required to complete this scale independently at the beginning and end of the treatment period. Patients were also monitored during the course of the trial using this scale. A small number of additional items, assessing rate of stool passage and interference with life activities, and recording changes in medications usage and fibre consumption, were included in the BSS for all patients to complete. Tests for validity and reliability of the scale are reported below.

(ii) Treatment Credibility Rating Scale

In order to assess the success of patient blinding a brief questionnaire was administered regularly throughout the treatment period. This four item scale was originally used to test credibility of different forms of psychological treatment[18] but has also been successfully used in acupuncture trials.[19,20] It has been shown to have good internal consistency and test-retest reliability. Tests for reliability, internal consistency, and construct validity are also reported here.

(iii) Statistical Analysis

Pearson product moment correlation was employed in the analysis of reliability and validity data. Factor analysis was also used to determine construct validity of the credibility scale. Outcome measures with categorical responses were analysed using Chi-square and Fisher's exact tests, For the bowel symptom scales analysis of variance was used to determine the differences between groups at baseline, at end of treatment and an follow-up. In each case the statistical assumptions were carefully considered, p values were all 2-tailed unless otherwise indicated, a level of significance was set at 0.05. Missing scale and item scores were not replaced.

Data are presented below according to an 'intention to treat' protocol, where patients who withdrew from the trial are recorded as having worsened (if appropriate) for categorical items only. Data for all other outcome measures are presented as per protocol analysis.

EXAMPLE 3

Results of the Study

A total of 78 subjects were recruited over an 18 month period: 35 were randomised into the placebo group and 43 into the standard treatment group. Fifteen patients (13%) withdrew during the four month course of the trial. A further two patients were withdrawn from the trial for commencing a variety of relevant medications during the treatment period. Patient data on entry is summarised in Table 5.

Table 5: Patient population characteristics pre-treatment and mean total bowel symptom scores as reported by patients and gastroenterologists at start and end of treatment period, and at a follow-up. (Standard deviation in brackets, n=subject numbers). $^x$p<0.10, $^{xx}$p<0.05, $^{xxx}$p<0.01, #p=0.75.

|  | Placebo group (n = 35) | Standard group (n = 43) | F statistic |
|---|---|---|---|
| Characteristic |  |  |  |
| Weight | 72.1(12.8) | 66.7(16.8) | 1.27 |
| Age | 45.0(13.9) | 47.6(15.1) | 0.39 |
| Gender (male:female) | 0.46 | 0.65 | NS# |
| Baseline data |  |  |  |
| Gastroenterologist total BSS score | 182.7(65.4) | 172.2(72.6) | 0.52 |
| Patient total BSS score | 191.2(69.4) | 189.7 (64.8) | 0.40 |
| End of treatment |  |  |  |
| Gastroenterologist total BSS score | 147.2 (86.6) (n = 30) | 70.9 (63.2) (n = 35) | 7.92$^{xxx}$ |
| Patient total BSS score | 150.0 (81.6) (n = 32) | 106.1 (73.7) (n = 38) | 3.79$^{xx}$ |
| At follow-up |  |  |  |
| Patient total BSS score | 155.7 (84.2) (n = 18) | 132.6 (90.2) (n = 35) | 2.41$^x$ |

Patient groups were similar in terms of age, weight and gender distributions. There were no significant differences between patients in the two treatment groups on entry in terms of total severity of symptoms as judged independently by both the patient and gastroenterologist, and no significant differences in duration of the disease as self-reported by patients. However, patients allocated to the placebo group did register a higher mean score for constipation, whilst patients allocated to the standard treatment group registered a higher mean score for diarrhoea. Compliance with medication was high as measured by a questionnaire item and by random pill counts, and did not differ between groups. Fibre and medication consumption did not alter significantly for any group during the treatment period.

(i) Reliability Testing

The reliability of the BSS (ie the consistency of the measure) was determined by a test-retest assessment during the run-in period prior to treatment commencing (week 0 to week 2). Patients were invited to complete the BSS during the initial interview with the gastroenterologist and then two weeks later at the clinical treatment centers prior to treatment commencing. Correlation between the first completion of the bowel symptom scale (BSS1) and the second (BSS2) was high for the total score (r=0.7, p<0.01, two-tailed) and for each individual symptom (bloating (r=0,8), pain (r=0.6), diarrhoea (r=0.8) and constipation (r=0.7)). The high test-retest reliability between the two scale scores indicates the test is reliable an repeated administration and that the patients' presentation of their condition was relatively stable.

The credibility scale was also examined for test-retest reliability. Correlation between the first and second administration of this scale was significant (r=0.6, p<0.01, two-tailed). The correlation coefficients for each of the four scale items fell in the range of 0.47 to 0.65. The internal consistency of the credibility scale was explored by examining inter-item correlations an each of the first two occasions. Inter-item correlations on both occasions were uniformly high and Cronbach's coefficient alpha (representing average inter-item correlations) was 0.87 and 0.86 for the first and second occasions, respectively.

(ii) Validity Testing

The visual analogue scales within the BSS had high face validity (100 mm lines with severity marked at the extreme right and absence of symptom marked at the extreme left), and have high content validity (in that they incorporate the key domains of interest—pain anid discomfort, bloating, constipation and diarrhoea). The items in the scale were also tested for concurrent validity against the gastroenterologist assessment at the commencement and at the end of the treatment period. At these times both patients and gastroenterologists completed the visual analogue scales independenltly. The gastroenterologist assessment of the patient correlated highly with the patient's own perception of severity of symptoms. (On both occasions Pearson's correlation coefficient was in the range of r=0.63 to r=0.84 for any one item (symptom) or for the total symptom score) (p<0.01 on all occasions).

The credibility scale was assessed for construct validity through a principal components factor analysis based on the first administration. The results revealed only one factor with an eigenvalue greater than 1 (2.89). This factor accounted for 72.2% of variance in this data set. All items had a high correlation with this first factor. This suggests that there was a satisfactory level of construct validity of this scale.

(iii) Main Outcome Measures

Five distinct outcome measures are reported here—total mean bowel symptom scales and global improvement as recorded by patients and gastroenterologists, and interference with life as recorded by patients. On all measures, patients receivng the standard herbal formulation of the present invention responded significantly better than patients in the placebo group.

(iv) Bowel Symptom Scales

The bowel symptom scales were completed by patients at various stages during the course of treatment including upon completion of the trial. An analysis of variance (ANOVA) test performed at the end of treatment demonstrated a significant difference between the mean total symptom scores for patients in each group, the standard herbal treatment patients responding significantly better compared to placebo (F=3,8; df 2, 96; p<0.05) (Table 5).

The bowel symptom scale was also completed by the gastroenterologist on reviewing the patient at the end of the treatment period. Analysis of variance showed a significant difference between the mean total symptom scores for patients in each group, with standard herbal treatment patients responding significantly better compared to placebo (F=7.9; df 2, 87; p<0.05).

Patients receiving the standard herbal formulations improved by 44% (according to patients) and 59% (according to gastroenterologists), in contrast to patients in the placebo group who improved 22% (according to patients) and 19% (according to gastroenterologists).

(v) Interference with Life

An item was included in the BSS asking patients to assess the degree of interference with life and activities. Responses allowed for a grade of severity of interference to be recorded. This item was included on each occasion the patient completed the BSS. Change in the severity score for this item was calculated for each patient. A significant association was found between the treatment groups and the change in grade of interference by the end of treatment (p=0.03, df=4, $X^2$=10.6). 63% of patients receivng the standard formulation stated treatment resulted in less interference in their lives and activities, in contrast to 37% of placebo patients.

(vi) Global Improvement

At the end of the trial both gastroenterologists and patients were asked whether they felt the IBS symptoms had improved, stayed the same or worsened (Table 6).

TABLE 6

Perception of improvement by treatment group (percentages of respondents in brackets)

| Compared to before trial | | Placebo group | Standard group |
|---|---|---|---|
| Patient response | Improved | 11 (33%) | 29 (76%) |
| Chi-square p = 0.007 | Stayed the same | 19 (57%) | 8 (21%) |
| | Worsened | 3 (9%) | 1 (3%) |
| Gastroenterologist response | Improved | 9 (30%) | 29 (78%) |
| Chi-square p = 0.002 | Stayed the same | 19 (63%) | 7 (19%) |
| | Worsened | 2 (7%) | 1 (3%) |

Asignificant association between the treatment group and how patients felt at the end of treatment was observed (p=0.007, df=4, $X^2$=14.3). 76% of patients receiving the standard formulation stated they had improved during treatment. In contrast, only 33% of patients receiving placebo stated they had improved during treatment.

The gastroenterologists' responses also demonstrated a significant association between the treatment group and how patients felt at the end of treatment (p=0.002, df=4, $X^2$=17.1). 78% of patients receiving the standard formulation were identified as having improved during treatment. In contrast, only 30% of patients receiving placebo perceived having improved during treatment.

There was significant correlation between patients' and gastroenterologists' assessment of global improvement and of total BSS scores at the beginning and end of the trial (all r>0.5, all significant to 0,01 level, 2-tailed).

(vii) Follow-up Assessment

The BSS was administered to patients one final time 14 weeks after completion of the course of treatment. Treatment codes were not revealed to patients until after completion of this final follow-up questionnaire, hence patients were still blinded. Blinding of patients was verified.

Patients still responded as having made notable improvement when compared to before the trial. A chi-square test performed on the patient responses demonstrated a significant association between the treatment group and how patients felt at the point of follow-up (p=0.02, df=4, $X^2$=11.5). 63% of patients who had received the standard formulation stated they still felt improved. Notably, 32% of patients who had received placebo stated they still felt improved.

Herbalism, acupuncture, homeopathy and manual therapies (eg osteopathy) frequently rely on a second diagnostic process distinct from western medicine and an high degree of interaction between the patient and practitioner during the treatment. The former leads to a clinical distinction between what seem to be similar diagnostic cases in western medicine (individualisation of therapy). The latter demands that the therapeutic intervention be continuously modified in response to patient feedback. Treatment needs to be tailored to the individual at the outset and also modified at differing stages of the patient's illness. Rigorous clinical trial methodology frequently imposes standardisation of treatment for trial subjects.

The present study has demonstrated that Chinese herbal medicine is effective in the management of irritable bowel syndrome with, in some cases, effects lasting up to 14 weeks after completion of treatment. At the outset of the study there were no significant differences between patients in each group. They were well matched for age, gender, weight, severity and duration of illness. Patients receiving standard herbal treatment demonstrated significantly better outcomes (both clinically and statistically) than patients receiving the placebo treatment an all five key outcome measures.

A conclusion can be drawn that Chinese herbal formulations of the present invention may offer substantial assistance to patients with irritable bowel syndrome and constitute an alternative treatment option for the management of IBS.

A person skilled in the art will understand that the therapeutic effects of the compositions result from a plurality of active agents in each herb which when combined, to act synergistically to enhance efficacy. It will also be understood that compositions comprising all or a selection of such active agents, preferably in pure form, are also contemplated herein, as are liquid formulations of the composition and formulations which are suitable for slow release administration. Thus it will be understood that the compositions of the invention can be administered orally, intravenously, topically or by other known means.

The invention may be embodied in various other forms which are understood by those skilled in the art.

REFERENCES

1. Drossman D A, Li Z, Andruzzi E, Temple R, Talley N J, Thompson W G, et al. U.S. householder survey of functional gastrointestinal disorders: prevalence, sociodemography and health impact. Dig Dis Sci. 1993;38:1569–1580.
2. Talley N J, Zinsrneister A R, Van Dyke C, Melton L J III. Epidemiology of colonic symptoms and the irritable bowel syndrome. Gastroenterology. 1991; 101,927–9343.
3. Heaton K W, O'Donnell L J D, Braddon F E M, Mountford R A, Hughes A O, Cripps P J. Irritable bowel syndrome in a British urban community: consulters and non-consulters. Gastroenterology. 1992;102:1962–1967.
4. Jones R, Lydeard S. Irritable bowel syndrome in the general population. BMJ. 1992;304:87–190.
5. Talley N J, Boyce P M, Owen B K, Newman P, Paterson K J, Initial validation of a bowel symptom questionnaire and measurement of chronic gastrointestinal symptoms in Australians. Aust N Z J Med. 1995;25:302–307.
6. Talley N J, Owen B K, Boyce P, Paterson K. Psychological treatments for irritable bowel syndrome: a critique of controlled treatment trials. Am J Gastroenterology. 1996;91:277–283.
7. Keien K B. Controlled treatment trials in the irritable bowel syndrome: a critique. Gastroenterology. 1988;95:232–241.
8. Bensoussan A, Myers S P. Towards a Safer Choice: the practice of Traditional Chinese Medicine in Australia. Sydney: University of Western Sydney Macarthur, 1996.
9. Yu Z X, Wang K & Li F P. Clinical trial of Chinese herbal capsule for 157 cases of irritable bowel syndrome. China Journal of Integrated Chinese and Western Medicine. 1991;11:170–171.
10. Liu Z K. Chinese herbal medicine treatment for 120 cases of irritable bowel syndrome. China Journal of Integrated Chinese and Western Medicine, 1990;10.615.

11. Shi Z Q. Combination treatment of Chinese and Western medicine for 30 cases of irritable bowel syndrome. China Journal of Integrated Chinese and Western Medicine. 1989;19:241.
12. Chen D Z. Tong Xie Yao Fang with additions in treating 106 cases of irritable bowel syndrome. Nanjing Medical University Journal. 1995;15:924.
13. Xu R L. Clinical realisations during the diagnosis and treatment of 55 cases of irritable bowel syndrome. Shanxi Journal of Traditional Chinese Medicine. 1995;11:10–11.
14. Anthony H M. Some methodological problems in the assessment of complementary therapy. In: Lewith G T, Aldridge D, eds. Clinical Research Methodology for Complementary Therapies. London: Hodder & Stoughton; 1993:108–121.
15. Bensoussan A. Contemporary acupuncture research: the difficulties of research across scientific paradigms. Amer J Acup. 1993;19:357–366.
16. Thompson W G, Creed F, Drossman D A, Heaton K W, Mazzacca G. Functional bowel disease and functional abdominal pain. Gastroenterology International. 1992;5:75–91.
17. Talley N J, Nyren O, Drossman D A, Heaton K W, Veldhuyzen van Zanten S J O, Koch M M, et al. The irritable bowel syndrome: toward optimal design of controlled treatment trials. Gastroenterology International. 1993;6:189–211.
18. Borkovec T D, Nau S D. Credibility of analogue therapy rationales. J Behav Ther Exp Psychiat. 1972;3:257–260.
19. Vincent C. Credibility assessment of trials in acupuncture. Complementary Medical Research. 1990;4:8–11.
20. Petrie J, Hazleman B. Credibility of placebo transcutaneous nerve stimulation and acupuncture. Clin Exp Rheumatol. 1985;3:151–153.
21. Kane J A, Kane S P, Jain S. Hepatitis induced by traditional Chinese herbs: possible toxic components. Gut 1995;36:146–147.

What is claimed is:

1. A composition comprising the herbs *Ledebouriellae Sesloidis, Bupleurum Chinense, Artemesiae Capillaris, Fraxini, Plantaginis, Paeoniae Lactiflorae* and *Schizandrae*.

2. A composition according to claim 1, which is formulated with powdered herbs.

3. A composition according to claim 1, which includes extracts of the herbs.

4. A composition according to claim 1, in a capsule or table dosage form.

5. A composition according to claim 1, further including pharmaceutically acceptable excipients, adjuvants, solvents, carriers, flavours, colourings or coatings.

6. A composition comprising at least two herbs selected from the group consisting of *Codonoposis Pilosulae, Atractylodis Macrocephalae, Poriae Cocos* and *Olycyrrhizae Uralensis*, any two herbs selected from the group consisting of *Agastaches seu Pogostemi, Magnoliae Officinalis, Citri Reticulatae* and *Saussureae sue Vladimiriae*, at least two herbs selected from the group consisting of *Phellodendri, Coptidis, Coicis Lacluyma-jobi, Zingiberis Offinicinalis* and *Angelicae Dehuricae*, and at least two herbs selected from the group consisting of *Ledebouriellae Sesloidis, Bupleurum Chinense, Artemesiae Capillaris, Fraxini, Plantaginis, Paeoniae Lactiflorae* and *Schizandrae*.

7. A composition according to claim 6, which is formulated with powdered herbs.

8. A composition according to claim 6, which includes extracts of the herbs.

9. A composition according to claim 6, in a capsule or tablet dosage form.

10. A composition according to claim 6, further including pharmaceutically acceptable excipients, adjuvants, solvents, carriers, flavours, colourings or coatings.

11. A composition comprising the herbs *Codonoposis Pilosulae, Agastaches seu Pogostemi, Ledebouriellae Sesloidis, Coicis Lachyrmna-jobi, Bupleurum Chinense, Artemesiae Capillaris, Atractylodis Macrocephalae, Magrioliae Officinalis, Citri Reticulatae, Zingiberis Offinicinalis, Fraxini, Poriae Cocos, Angelicae Dehuricae, Plantaginis, Phellodendri, Glycyrrhizae Uralensis, Paeoniae Lactiflorae, Saussureae seu Vladimirae, Coptidis* and *Schizandrae*.

12. A composition according to claim 11, which is formulated with powdered herbs.

13. A composition according to claim 11, which includes extracts of the herbs.

14. A composition according to claim 11, in a capsule or tablet dosage form.

15. A composition according to claim 11, further including pharmaceutically acceptable excipients, adjuvants, solvents, carriers, flavours, colourings or coatings.

16. A method of treating gastrointestinal disorders comprising administering to a subject requiring such treatment a therapeutically effective amount of a composition according to claim 1, thereby treating the disorder.

17. A method according to claim 16, wherein the gastrointestinal disorder to be treated is Irritable Bowel Syndrome (IBS).

18. A method according to claim 16, wherein the treatment is administered orally.

19. A method according to claim 16, wherein the treatment is therapeutic or prophylactic and may be administered in a single bolus dose, multiple doses or via a slow release device.

20. A method of treating gastrointestinal disorders comprising administering to a subject requiring such treatment a composition according to claim 6, thereby treating the disorder.

21. A method according to claim 20, wherein the gastrointestinal disorder to be treated in Irritable Bowel Syndrome (IBS).

22. A method according to claim 20, wherein the treatment is administered orally.

23. A method according to claim 20, wherein the treatment is therapeutic or prophylactic and may be administered in a single bolus dose, multiple doses or via a slow release device.

24. A method of treating gastrointestinal disorders including the administration to a subject requiring such treatment a composition according to claim 11, thereby treating the disorder.

25. A method according to claim 24, wherein the gastrointestinal disorder to be treated is Irritable Bowel Syndrome (IBS).

26. A method according to claim 24, wherein the treatment is administered orally.

27. A method according to claim 24, wherein the treatment is therapeutic or prophylactic and may be administered in a single bolus dose, multiple doses or via a slow release device.

* * * * *